United States Patent
Ammar et al.

(10) Patent No.: US 10,942,098 B2
(45) Date of Patent: Mar. 9, 2021

(54) METHOD AND SYSTEM FOR ANALYZING AT LEAST A ROCK SAMPLE EXTRACTED FROM A GEOLOGICAL FORMATION

(71) Applicant: Geoservices Equipements, Roissy en France (FR)

(72) Inventors: Mahdi Ammar, Roissy-en-France (FR); Jerome Breviere, Roissy-en-France (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 197 days.

(21) Appl. No.: 16/107,476

(22) Filed: Aug. 21, 2018

(65) Prior Publication Data

US 2019/0064039 A1 Feb. 28, 2019

(30) Foreign Application Priority Data

Aug. 25, 2017 (EP) .................... 17290108

(51) Int. Cl.
| | |
|---|---|
| *G01N 1/44* | (2006.01) |
| *G01N 21/01* | (2006.01) |
| *G01N 33/24* | (2006.01) |
| *G01N 1/34* | (2006.01) |
| *G01N 21/552* | (2014.01) |

(Continued)

(52) U.S. Cl.
CPC .............. *G01N 1/44* (2013.01); *G01N 1/34* (2013.01); *G01N 21/01* (2013.01); *G01N 33/241* (2013.01); *G01N 21/3563* (2013.01); *G01N 21/552* (2013.01); *G01N 21/65* (2013.01); *G01N 21/718* (2013.01); *G01N 2001/2866* (2013.01);

(Continued)

(58) Field of Classification Search
CPC ........ G01N 1/34; G01N 21/01; G01N 33/241; G01N 1/44
See application file for complete search history.

(56) References Cited

U.S. PATENT DOCUMENTS

| | | | | |
|---|---|---|---|---|
| 2,583,276 | A | * | 1/1952 | Patnode ............... G01N 33/241 324/449 |
| 4,687,523 | A | * | 8/1987 | Hall ........................ G01N 1/34 134/30 |

(Continued)

FOREIGN PATENT DOCUMENTS

| | | | | |
|---|---|---|---|---|
| EP | 3588083 A1 | * | 1/2020 | ............. G01N 33/24 |
| WO | WO-9517982 A1 | * | 7/1995 | ........... E21B 21/066 |
| WO | 2015084784 A1 | | 6/2015 | |

OTHER PUBLICATIONS

Glorioso et al., "Unconventional Reservoirs: Basic Petrophysical Concepts for Shale Gas," SPE-153004 (Year: 2012).*

(Continued)

*Primary Examiner* — John Fitzgerald

(57) ABSTRACT

The disclosure relates to a method of analyzing at least a rock sample extracted from a geological formation. The method comprises:
- heating the at least one rock sample under inert atmosphere with a temperature below 300° C. and with a flow of inert gas to remove contaminants,
- analyzing at least one of the decontaminated rock samples and determining at least a property relative to non-volatile organic matter contained in the geological formation based on the analysis.

20 Claims, 4 Drawing Sheets

(51) Int. Cl.
   *G01N 21/65* (2006.01)
   *G01N 21/35* (2014.01)
   *G01N 21/3563* (2014.01)
   *G01N 21/71* (2006.01)
   *G01N 1/28* (2006.01)

(52) U.S. Cl.
   CPC ............... *G01N 2021/3595* (2013.01); *G01N 2223/616* (2013.01)

(56) References Cited

U.S. PATENT DOCUMENTS

| | | | | |
|---|---|---|---|---|
| 4,880,528 | A * | 11/1989 | Westhoff | C10G 1/02 208/409 |
| 5,082,787 | A * | 1/1992 | Nolte et al. | |
| 5,180,556 | A * | 1/1993 | Nolte et al. | |
| 5,286,651 | A * | 2/1994 | Smith | G01N 33/241 436/32 |
| 5,916,434 | A * | 6/1999 | Ripley | B09C 1/06 208/407 |
| 9,651,461 | B2 * | 5/2017 | Snape | B08B 3/022 |
| 10,360,282 | B2 * | 7/2019 | Rasmus | G06F 17/11 |
| 10,578,600 | B2 * | 3/2020 | Inan | G01N 1/34 |
| 10,656,134 | B2 * | 5/2020 | Karoum | G01N 31/12 |
| 2012/0234360 | A1 * | 9/2012 | Snape | G01N 33/24 134/26 |
| 2013/0269933 | A1 | 10/2013 | Pomerantz et al. | |
| 2013/0273661 | A1 * | 10/2013 | Pomerantz | G01N 33/241 436/29 |
| 2014/0157870 | A1 * | 6/2014 | Kornacki | G01N 33/2835 73/23.38 |
| 2015/0212235 | A1 * | 7/2015 | Barwise | G01V 99/005 703/2 |
| 2015/0308264 | A1 * | 10/2015 | Zuo | E21B 49/088 702/6 |
| 2016/0084756 | A1 * | 3/2016 | Herron | G01N 21/3563 250/254 |
| 2016/0186556 | A1 * | 6/2016 | Rasmus | G06F 17/11 703/2 |
| 2016/0349174 | A1 * | 12/2016 | Washburn | G01N 33/28 |
| 2017/0031051 | A1 * | 2/2017 | Song | G01V 3/14 |
| 2017/0045491 | A1 * | 2/2017 | Karoum | G01N 33/241 |
| 2017/0191908 | A1 * | 7/2017 | Snape | B08B 3/022 |
| 2017/0329045 | A1 * | 11/2017 | Myers | G06T 7/0004 |
| 2018/0195383 | A1 * | 7/2018 | Smith | E21B 49/08 |
| 2019/0025198 | A1 * | 1/2019 | Washburn | G01N 29/2418 |
| 2019/0056375 | A1 * | 2/2019 | Inan | G01N 1/44 |
| 2019/0079065 | A1 * | 3/2019 | Aboussou | G01N 31/12 |
| 2019/0107522 | A1 * | 4/2019 | Romero-Sarmiento | G01N 33/241 |
| 2019/0317070 | A1 * | 10/2019 | Inan | B09C 1/065 |
| 2019/0339175 | A1 * | 11/2019 | Snape | G01N 1/34 |
| 2020/0003694 | A1 * | 1/2020 | Sauerer | G01N 33/2823 |

OTHER PUBLICATIONS

Alfonsi et al., Green chemistry tools to influence a medicinal chemistry and research chemistry based organization, The Royal Society of Chemistry, Green Chem, vol. 10, pp. 31-36, 2008.

Romero-Sarmiento, et al., New Rock-Eval Method for Characterization of Unconventional Shale Resource Systems, published by IFP Energies nouvelles, Oil Gas Science Technology, vol. 71, No. 3, Article 37, May-Jun. 2016, 9 pages.

* cited by examiner

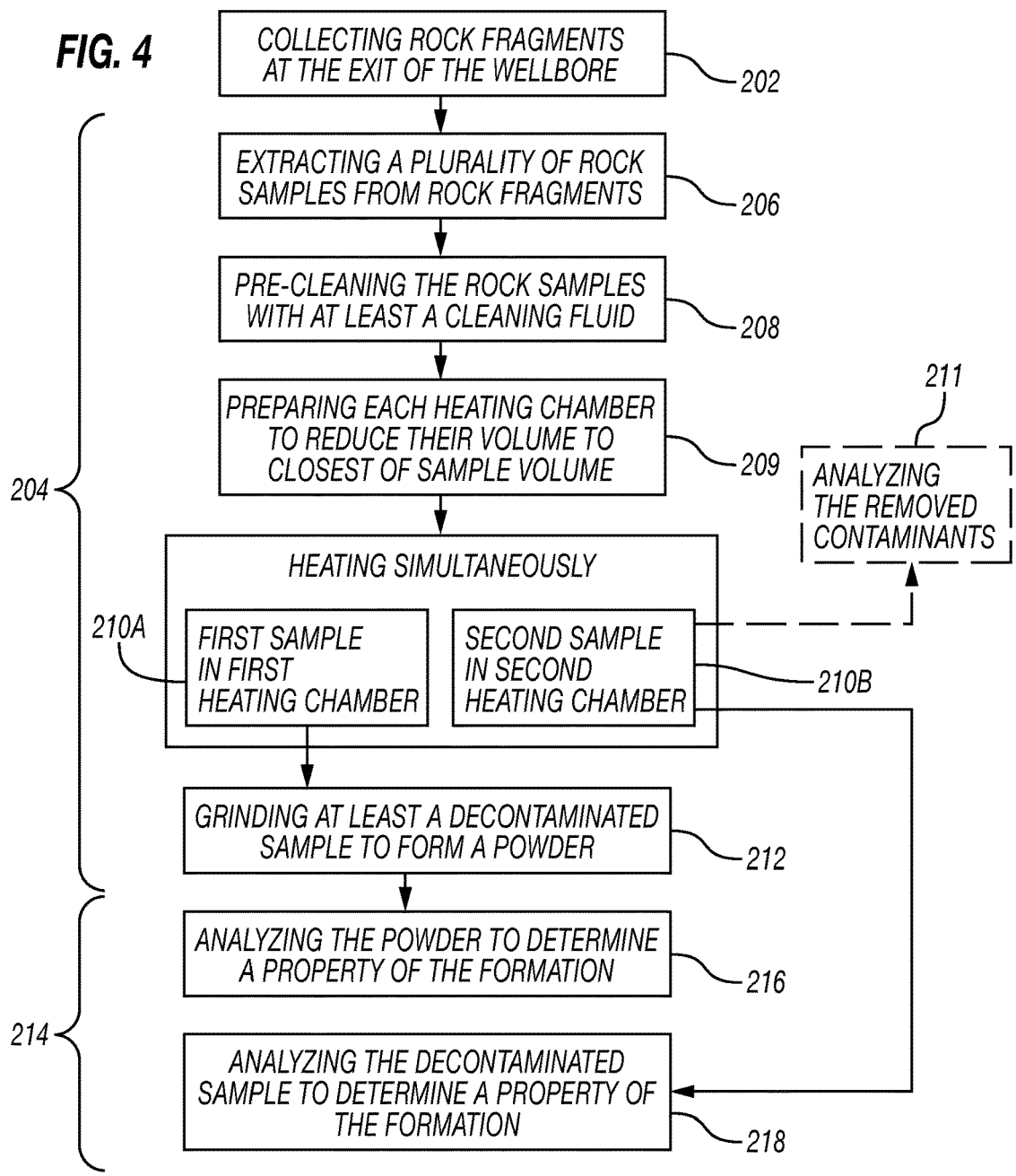

METHOD AND SYSTEM FOR ANALYZING AT LEAST A ROCK SAMPLE EXTRACTED FROM A GEOLOGICAL FORMATION

BACKGROUND

The disclosure relates to a method and system for analyzing a rock sample and more specifically to prepare the rock sample in view of its analysis.

When drilling a wellbore in a geological formation, it has always been sought to identify the nature of the geological formation in order to evaluate a potential for oil and/or gas exploitation. The nature of the formation may be identified via downhole tools able to log the formation directly downhole or via rock samples recovered from the geological formation such as core or drill cuttings.

There has been a lot of efforts to analyze the drill cuttings which are particularly easy to recover as they are exiting the wellbore and coming back to the surface with drilling fluid circulating in the wellbore. Such drill cuttings may be mapped in depth with the wellbore and give valuable information about the formation at that depth.

The analysis of drill cuttings is already performed in the field. In particular, drill cuttings are analyzed to determine several properties such as their mineralogical composition, elemental composition or total organic content. Analysis techniques that are used are for instance X-Ray Diffraction, X-Ray Fluorescence, thermal analysis with analyzers called TOC (Total Organic Carbon) analyzers, and DRIFTS (Diffuse Reflectance Infrared Fourier Transform) spectroscopy.

However, these drill cuttings being mixed with drilling fluid on their way out of the wellbore, they are contaminated with the drilling fluid which makes it more difficult to get valuable information out of their analysis. This is particularly true when the wellbore is drilled with oil-based mud in which case it is difficult to discriminate the oil coming from the drilling fluid and from the formation.

There is therefore a need for preparing the sample before analyzing it in order to decontaminate it. This may be the case especially when the analysis aims at determining a property relative to the non-volatile organic matter contained in the sample, such as TOC (Total Organic Content). In the past, a method has been developed by Schlumberger for preparing the sample. This method comprises cleaning the drill cuttings with a solvent such as pentane before grinding the drill cuttings and cleaning it once more with the solvent after grinding. The TOC may afterwards be determined via DRIFTS spectroscopy. Several embodiments of such a method are for instance disclosed in US patent application No. 2013/0269933. This method cleans the drill cuttings in an appropriate way to remove the contamination from the drilling fluid.

SUMMARY

The disclosure relates to a method of analyzing a rock sample extracted from a geological formation. It comprises heating the sample under inert atmosphere with a temperature below 300° C. and with a flow of inert gas to remove contaminants, and analyzing the decontaminated rock sample and determining a property relative to non-volatile organic matter contained in the geological formation based on the analysis.

It also relates to a system for analyzing a rock sample extracted from a geological formation for analysis. The system includes an oven installation a heating chamber for receiving the rock sample, a heater for heating the chamber, a controlling unit so that the temperature inside the chamber is below 300° C. and a flow generator for providing a flow of inert gas into the chamber. The system also includes an analyzer configured for analyzing the decontaminated sample in order to determine at least a property relative to non-volatile organic matter contained in the geological formation based on the analysis The method according to the disclosure gives equivalent results as the above-mentioned method in terms of cleaning efficiency. The setup is furthermore simple and may be installed easily on a rig and even in an explosive environment without significant additional requirements due to improved safety conditions as there is no flammable chemicals are needed for the preparation of the sample.

The methods and system according to the disclosure therefore enables to obtain information relative to the formation properties directly at the rig site.

BRIEF DESCRIPTION OF THE DRAWINGS

Various aspects of this disclosure may be better understood upon reading the following detailed description and upon reference to the drawings in which:

FIG. 3 is a flowchart of a method according to an embodiment of the disclosure;

FIG. 4 is a flowchart of a method according to another embodiment of the disclosure;

DETAILED DESCRIPTION

One or more specific embodiments of the present disclosure will be described below. These described embodiments are examples of the presently disclosed techniques. Additionally, in an effort to provide a concise description of these embodiments, some features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.'

Figure 1:
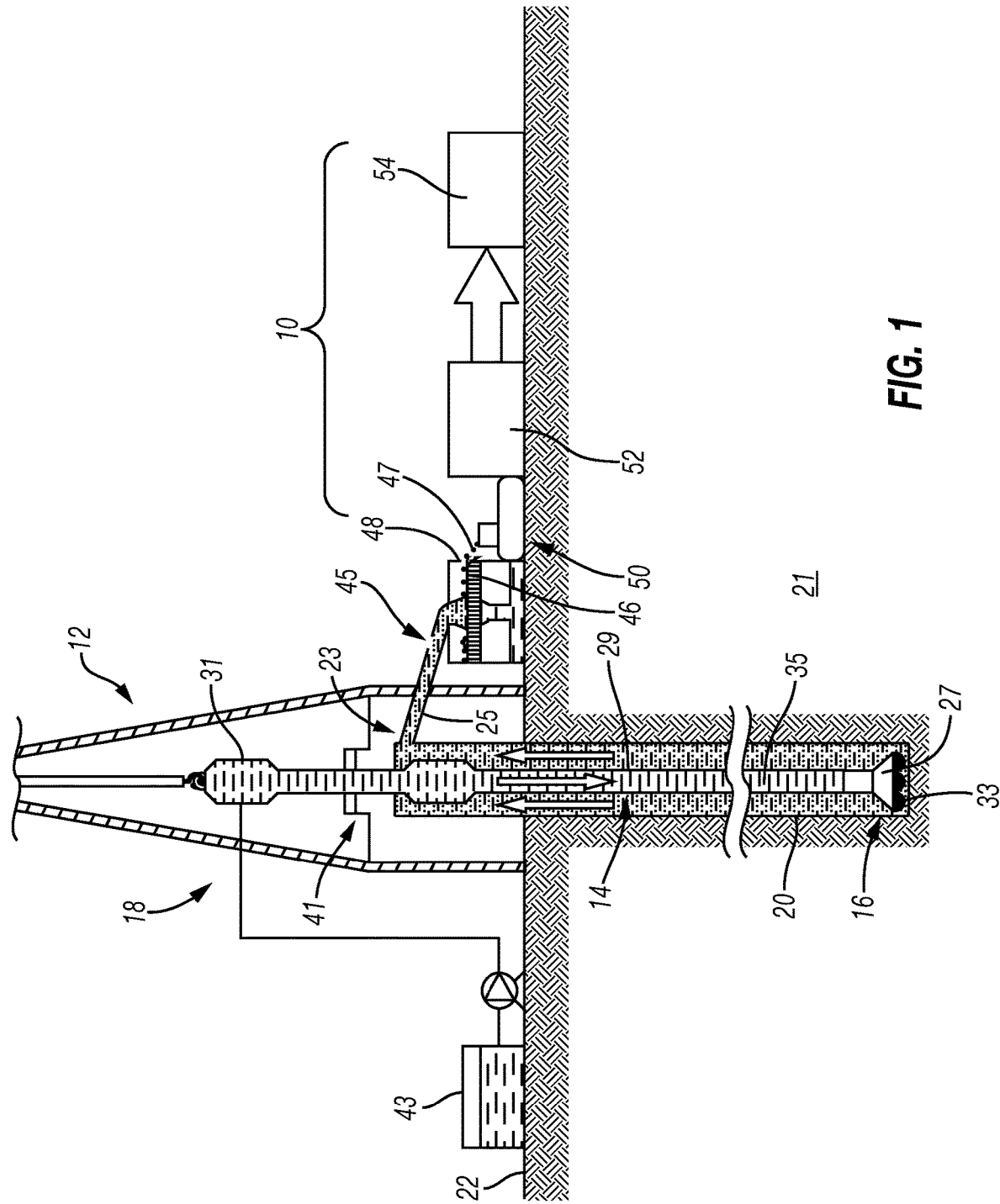
FIG. 1 is a schematic drawing of a system of analyzing drill cuttings according to an embodiment of the disclosure, shown at the rig site

FIG. 1 discloses a system 10 for analyzing drilling cuttings, as described above, that may be included in a drilling installation 12 for a fluid production well, such as a hydrocarbon production well.

Such an installation 12, illustrated on FIG. 1, comprises: a rotary drilling tool 14 drilling a cavity 16; a surface installation 18, where drilling pipes are placed in the cavity 16; and the system 10 as mentioned above.

A borehole 20, delimiting the cavity 16, is formed in the substratum 21 by the rotary drilling tool 14. At the surface 22, a well head 23 having a discharge pipe 25 closes the borehole 20.

The drilling tool 14 comprises a drilling head 27, a drill string 29 and a liquid injection head 31.

The drilling head 27 comprises a drill bit 33 for drilling through the rocks of the substratum 21. It is mounted on the lower portion of the drill string 29 and is positioned in the bottom of the drilling pipe 20.

The drill string 29 comprises a set of hollow drilling pipes. These pipes delimit an internal space 35 which makes it possible to bring a drilling fluid from the surface 22 to the drilling head 27. To this end, the liquid injection head 31 is screwed onto the upper portion of the drill string 29.

The drilling fluid is a drilling mud, in particular a water-based or oil-based drilling mud.

The surface installation 18 comprises a support 41 for supporting the drilling tool 14 and driving it in rotation, an injector 43 for injecting the drilling fluid and a shale shaker 45. The drilling fluid circulates downwards in the inner space 35, getting out of the inner space 35 at the bit 33 and flowing upwards in the cavity 16 to the surface, bringing along drilling residues.

The injector 43 is hydraulically connected to the injection head 31 in order to introduce and circulate the drilling fluid in the inner space 35 of the drill string 29.

The shale shaker 45 collects the drilling fluid charged with the drilling residues, known as drill cuttings, said drilling fluid flowing out from the discharge pipe 25. The shale shaker comprises a sieve 46 allowing the separation of the solid drill cuttings 47 from the drilling mud. The shale shaker 45 also comprises an outlet 48 for evacuating the drill cuttings 47.

The drill cuttings 47 have been separated from the drilling fluid, but, as explained above, they have been mixed with drilling fluid while they were going back to surface for several hours and drilling fluid has therefore infiltrated the cuttings or contaminated so that there is a need for cleaning the drill cuttings.

The analysis system 10 according to an embodiment of the disclosure may be situated at the outlet of the shale shaker 45 and comprises for instance a sampler 50 for collecting rock fragments of drill cuttings from the outlet 48 of the shale shaker 45; a preparation unit 52 for preparing the samples obtained from the rock fragments for analysis; and an analysis unit 54 for analyzing the samples. The preparation and analysis units 52 and 54 have been represented here at the well site but may be situated away in any other location, for instance at the well site in a mud logging cabin or remotely from the well site, in which case the collected rock fragments are sent away from the wellbore.

When the preparation and analysis unit are at the well site, it may be possible that all or part of the preparation and analysis operations are automated so as to provided an unmanned analysis system.

The analysis unit 54 may comprise one or several analyzers for estimating at least one property of the formation from which the cuttings are originated. It includes an apparatus for measuring a characteristic of the sample enabling to determine a property relative to non-volatile organic matter contained in the sample, such as TOC or thermal maturity. Such apparatus may be an infrared spectrometer (such as a DRIFTS apparatus—Diffuse Reflectance Infra-Red Fourier Transform Spectrometry) or a thermal analyzer (TOC analyzer).

The analysis unit may also include an apparatus for determining a mineralogical composition of the sample and/or an apparatus for determining an elemental composition of the formation (such as XRF—X-Ray Fluorescence). A same apparatus may sometimes enable to obtain several properties. Of course, this particular analysis unit is exemplary and it may comprise only one apparatus, or more than three, for determining the above-mentioned properties of the formation and/or other properties. For instance, other apparatuses that may be used are infrared spectrometry apparatuses such as transmission FTIR (Fourier Transform Infra-Red) Spectroscopy, ATR (Attenuated Total Reflectance) spectroscopy, Laser Induced-Breakdown Spectroscopy (LIES), Raman spectroscopy, X-Ray analysis apparatuses such as X-Ray Diffraction (XRD), Energy Dispersive X-Ray (EDX), Wavelength Dispersive X-Ray (WDX).

Figure 2:
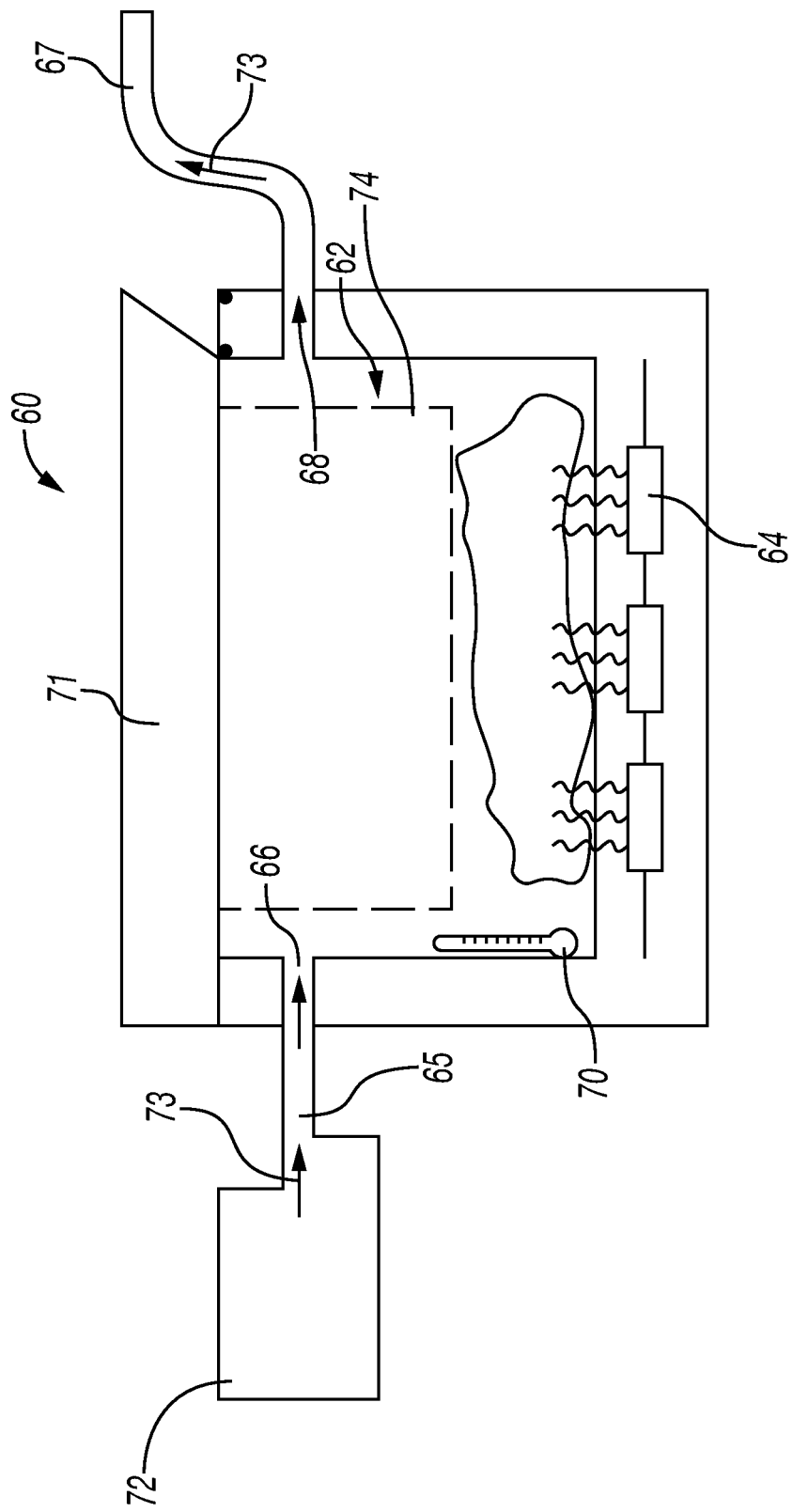
FIG. 2 is a schematic drawing of an element of the analysis system of FIG. 1, according to an embodiment of the disclosure

The preparation unit 52 is represented on FIG. 2. It comprises an oven installation 60 having a heating chamber 62, a heater 64 and a gas inlet 66 as well as a gas outlet 68. The gas inlet is connected to an inlet pipe 65 and the gas outlet 68 is connected to an outlet pipe 67. It also comprises a temperature sensor 70 for measuring temperature in the heating chamber and a pressure sensor for measurement an inlet pressure of the gas (not shown), as well as a temperature and pressure controller, all of which are well-known in the art and will not be detailed further. The heating chamber may have a volume that is below 1 L, or below 0.5 L but has a volume above 0.1 L to enable to receive samples of several grams such as between 1 and 30 grams while keeping a good control of the temperature. The heater may be for instance an electrical resistance but any other appropriate heater may be used. The oven installation also comprises a lid 71 for opening and closing the heating chamber 62 and introducing the sample in the heating chamber and removing it from the chamber. Of course, the heating chamber is thermally insulated from the outside by any appropriate way (seals, architecture of the chamber, etc.).

A carrier gas source 72 is connected to the gas inlet 66 upstream from the gas inlet via the inlet pipe 65. The carrier gas source may be a pressurized source. The carrier gas is an inert gas such as nitrogen, argon or helium. The outlet pipe 67 may be come out directly outside of the oven so that the gas outlet is connected with the atmosphere. Alternatively it may also be connected to a suction pump. The oven installation is configured so that the gas pressure at the gas source is above the gas pressure at the outlet of the outlet pipe 67 so that a flow of carrier gas 73 flows from the gas carrier source 72 to the heating chamber 62 and next to the outlet pipe 67.

The oven installation 60 may also include at least a removable spacer 74 that is shown in dotted line and is represented in the drawing as attached to the lid 71. This spacer enables to reduce the volume of the chamber so as to maximize the proportion of the volume occupied by the sample. Depending on the size of the sample, one or several spacers may be introduced in the chamber, fixed at the bottom of the chamber, which enable an easy manipulation of the sample. However, the spacers may be fixed alternatively or additionally to the lid as represented in the figure, and/or to the walls of the chambers. Of course, the oven installation may include a set of spacers of different sizes and shapes, all of them not being introduced simultaneously in the chamber, only the ones enabling to close the lid while the sample is in the chamber while maximizing the volume reduction being chosen at the introduction of the sample in the oven installation.

In an embodiment of the disclosure (not shown), the oven installation includes a plurality of heating chambers. In this configuration, the oven installation may comprise one heater and temperature controller for the whole installation.

The preparation unit 52 may also comprise a grinder for forming a powder with the sample. It may also comprise a sieve for sorting rock fragments collected at the shale shaker and selecting the fragment in a predetermined size range as the rock sample that will be analyzed. It may also include a cleaning unit for cleaning the fragments or samples. The cleaning unit may for instance include a cleaning fluid source and cleaning fluid jet pump for projecting the cleaning fluid on the fragments or samples. The cleaning fluid may for instance be pressurized water and/or a core base of the drilling fluid to which the cuttings were mixed, ie oil for oil based mud.

An analysis method 100 of a rock sample according to a first embodiment of the disclosure will now be described in view of FIG. 3. The rock sample may be a drill cutting collected at the exit of the wellbore. The method includes (block 102) heating the rock sample under inert atmosphere with a temperature below 300° C. and with a flow of inert gas to remove contaminants from the sample. This operation may be performed with the oven installation 60 as disclosed in relationship with FIG. 2. The temperature is chosen below 300° C. in order to be able to decontaminate the samples from the drilling fluid that has invaded the sample but not from the heavier components coming from the formation. For instance, the solid part of the organics matter in the rock, called kerogen, is not affected by this process. The temperature may be configured so as to be constant during the whole heating operation or so that the temperature ramps up from a first temperature to the second temperature. The temperature may also be chosen in view of the type of mud that has been used to drill the wellbore. Indeed, if the drilling fluid is a water-based drilling fluid, the drill cuttings are less contaminated than when the wellbore is drilled with oil-based drilling fluid and the temperature may then be lower. The flow of inert gas may be a flow of nitrogen for instance. The flow may be above 100 mL/min, for instance 200 mL/min so that the carrier gas and the gas extracted from the rock sample are carried away from the heating chamber 62 from the oven installation 60. The carrier gas may be introduced in the chamber with a pressure above the atmospheric pressure, which may facilitate the entry of the carrier gas in the pores of the rock sample. The heating operation may last less than 30 minutes. On top of the decontamination, the heating operation enables to dry the sample so that there is no need of a separate drying operation. Indeed, the drying operation is critical because measurement is sensitive to adsorbed water but may be avoided with the method according to the disclosure. The method according to the first embodiment then comprises analyzing (block 104) the decontaminated sample so as to derive from the sample at least a property of the formation, namely characteristic of the non-volatile organic matter contained in the sample and hence in the formation. Such property may be a thermal maturity and/or a Total Organic Content. It may be measured via one or more of DRIFTS (Diffuse Reflectance Infrared Transform Spectroscopy), FTIR (Fourier Transform Infra-Red) Spectroscopy, ATR (Attenuated Total Reflectance) spectroscopy, Raman spectroscopy. For some of these analysis and for instance the DRIFTS analysis, the method may also comprise (block 106) grinding the sample before analyzing it so as to form a powder from the decontaminated sample. Indeed, for some of the above-mentioned analysis, a more accurate measurement is obtained by using a powder.

A method of analysis 200 of a rock sample according to another embodiment of the disclosure will be described according to FIG. 4.

The method of analysis 200 includes collecting rock fragments at the exit of the wellbore, for instance at the shale shaker 45 (block 202). The rock fragments are then associated to a depth of the wellbore at which they have been separated from the rest of the formation due to the drilling of the formation, the depth being computed as a function of the lag time. The method then includes a preparation (block 204) that comprises extracting a plurality of rock samples from rock fragments (block 206), for instance by sieving the rock fragments so that the rock fragments selected for analysis are only the fragments having predetermined dimensions. The plurality of rock samples may then be pre-cleaned with at least a cleaning fluid (block 208). The cleaning operation may for instance be performed by immersing the samples in a bath of the cleaning fluid solution or to project the pressurized cleaning fluid on the plurality of rock samples thanks to one or several jet pumps. The cleaning fluid may include water and/or the core base of the drilling fluid, ie oil if the drilling fluid is an oil-based fluid. The pre-cleaning enables to remove mostly the additives of the drilling fluid. The method then includes performing simultaneously the heating operations as described above for several samples (block 210A, 210B). Simultaneously indicates that two samples may be heated during at least a common time period but the common time period may be only part of the total heating period for each of the sample. For instance, the heating operation for a first sample may be triggered before the heating operation for a second sample. The samples may be included in a same heating chamber but to avoid cross-contamination, it is preferred to use an oven installation having several heating chambers. The method includes, before heating the samples, preparing the or each heating chamber (block 209) by introducing in each chamber one or more spacers 74 so that the volume of the chamber is reduced as much as possible once it contains the sample, in order to maximize the portion of the volume of the chamber occupied by the sample, which also increases efficiency of the decontamination.

The method may also comprise analyzing the contaminants removed from one or more of the samples (block 211). This is considered as a classical thermal extraction method and the analysis may be performed via gas chromatography and mass spectrometry or Flame Ionization Detector (FID). This may give additional information on the drilling fluid or the formation, for instance identifying the formation oil signature, or monitoring the mud composition when the mud is oil-based.

The preparation method may then include grinding a decontaminated sample once it has been removed from the oven (block 212). Only one of the samples may be ground and the other may remain intact for analysis after being removed from the oven installation (ie not ground). Alternatively, only one portion of the sample may be ground while the other portion remain intact. Of course, this is exemplary and both samples may undergo the exact same preparation. They may be heated simultaneously, either with the heating being triggered simultaneously and ending simultaneously or with the heating period overlapping but not being triggered or not being stopped simultaneously. The method may also include heating more than two samples simultaneously.

The method may then include analyzing the obtained samples (block 214) in order to obtain from at least one sample a property regarding the non-volatile organic matter in the sample. In the following, both samples are not submitted to the same measurements but alternatively the method may comprise analyzing both samples in exactly the same way.

The analysis may for instance include introducing the powder obtained at block 212 in a first measurement apparatus and measuring a characteristic of the powder (block 216). This measurement apparatus may be for instance a DRIFTS measurement apparatus or a thermal analysis, such as the analysis disclosed in patent application WO2015/084784 The measured characteristic may for instance include a reflected spectrum (for DRIFTS). Each of the measured characteristic enable to derive a property of the formation such as a property relative to the non-volatile organic content in the formation. Such property may be a Total Organic Content. The DRIFTS measurement may additionally obtain the thermal maturity of the non-volatile organic matter. From the DRIFTS measurements, additional properties of the formation such as the mineralogy may also be derived.

The analysis may also include (block 218) introducing the decontaminated sample (that has not been ground) in a second measurement apparatus to measure a characteristic of the decontaminated sample. This characteristic may also enable to derive a property of the formation such as a property relative to the non-volatile organic content, or it may enable to derive another property of the formation such as elemental composition or mineralogical composition. The second measurement apparatus may for instance be a XRF measurement apparatus which will enable to derive information relative to the elemental composition of the formation.

Of course, the analysis operation may comprise one or more other analysis to derive one or several other properties of the formation. One prepared sample may be for instance introduced in several measurement apparatus in a row as several of the above-mentioned measurements are not destructive. The prepared sample may also be splitted in several portions that are analyzed separately.

Figure 5:
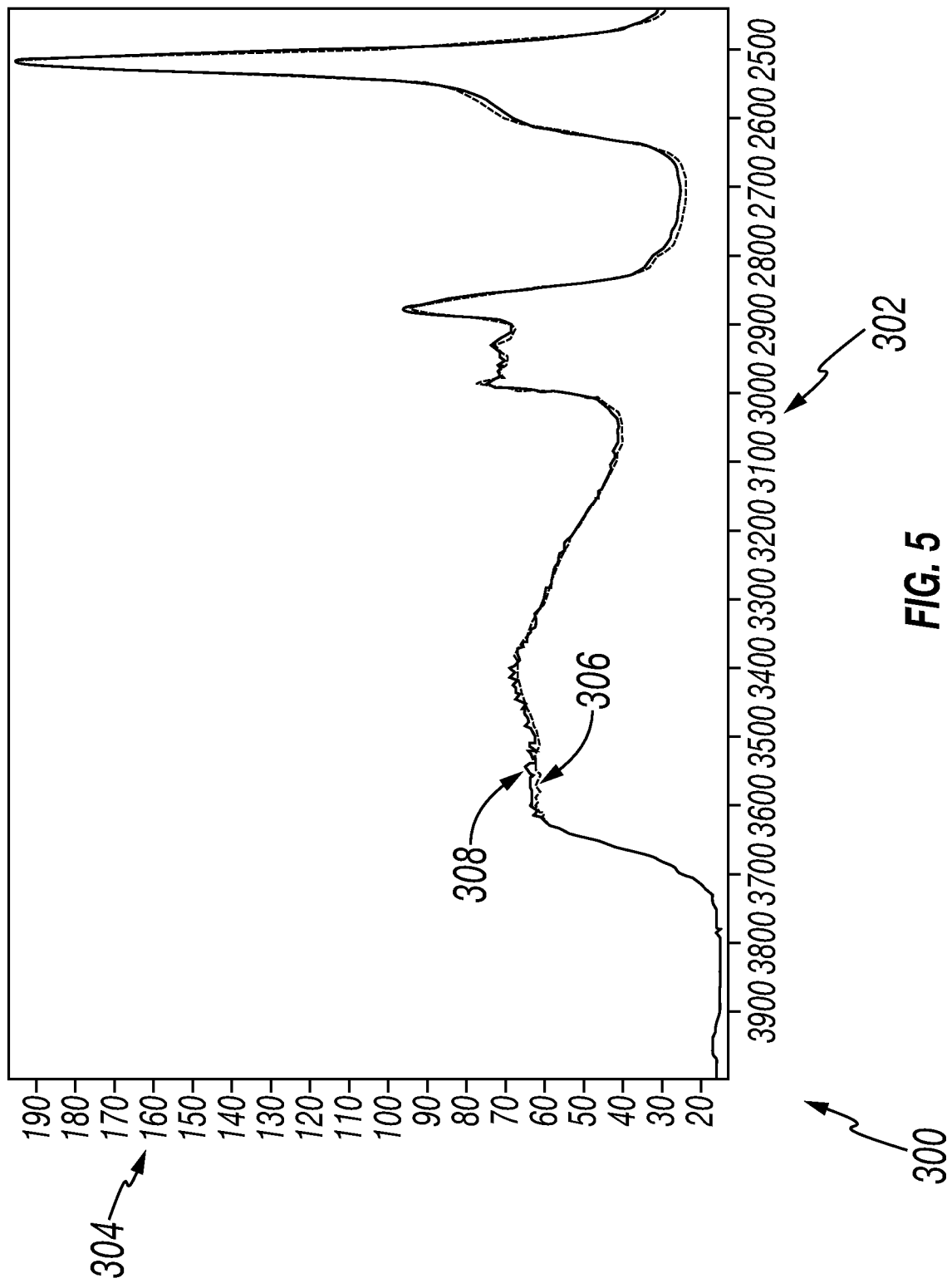
FIG. 5 is a plot showing a DRIFTS spectrum obtained from a sample by performing the method according to the disclosure compared to a spectrum obtained by performing a conventional method.

FIG. 5 shows a plot 300 of comparative spectra obtained from a DRIFTS apparatus (abscissa 302 is the wavenumber and ordinate 304 is intensity of the reflected light). Both spectra are relative to cuttings extracted from a same batch of cuttings (originating from the same depth). First spectrum 306 (grey curve) is obtained from a first sample prepared with the conventional method cited in the background section while second spectrum 308 (blue curve) is obtained from a second sample prepared with preparation operation 204 according to the disclosure. It can be observed that the spectra are analogous and that the cleaning efficiency of the method according to the disclosure is the same as the one of the spectrum prepared according to the conventional method. The method according to the disclosure is therefore as efficient as background methods. Further, it is easy to implement at a rig site as it does not raise any concern regarding safety.

While the invention has been disclosed with respect to a limited number of embodiments, those skilled in the art, having the benefit of this disclosure, will appreciate numerous modifications and variations there from. It is intended that the appended claims cover such modifications and variations as fall within the true spirit and scope of the invention.

The disclosure generally relates to a method of analyzing at least a rock sample extracted from a geological formation. The method comprises heating the at least one rock sample under inert atmosphere with a temperature below 300° C. and with a flow of inert gas to remove contaminants, analyzing at least one of the decontaminated rock samples and determining at least a property relative to non-volatile organic matter contained in the geological formation based on the analysis.

The method may also include grinding the sample once heated to form a powder. In this case, analyzing the rock sample includes analyzing the powder.

Regarding the inert gas of the flow, it may contain nitrogen, argon or helium. An inlet pressure of the flowing inert gas is superior to atmospheric pressure, in particular to 20 psi, preferably to 40 psi. The flow of inert gas is above 100 mL/min The rock sample may be heated during less than 30 minutes. Indeed, the method enables such decontamination after a heating period that is relatively short.

The rock sample may be placed in a chamber during heating, wherein the volume of the heating chamber is below 0.1 L. The heating chamber volume may be reduced with at least one spacer, preferably to minimize the empty volume of the chamber. It may enhance the decontamination and/or reduce the time necessary to reach a predetermined level of decontamination.

A plurality of rock samples may also be heated simultaneously in a plurality of respective heating chambers, which also enhances the efficiency of the preparation method and enable to initiate more analysis simultaneously.

The method may be devoid of drying the sample between the heating and the analysis. Indeed, the heating of the sample in order to decontaminate it also dries the sample which eliminates the need of a further separate drying operation.

The rock sample that is decontaminated and analyzed weights between 1 and 50 g. Indeed, the method according to the disclosure enables to deal with such samples The method may include, before heating, collecting a plurality of rock fragments and sieving the rock fragments to select one or more rock sample. It may also include, before heating, cleaning the rock sample, wherein the cleaning is performed with pressurized water or oil.

The rock sample may comprise drill cuttings recovered at the exit of the wellbore mixed with drilling fluid.

The method may comprise heating the rock sample at a maximum temperature of 200° C. when the drilling fluid is water-based and/or heating the rock sample at a maximum temperature of 300° C. when the drilling fluid is oil-based. The type of drilling fluid should then be identified and the temperature of the controller may be adjusted in view of the drilling fluid type.

The property relative to the non-volatile organic matter may include total organic content (TOC) and/or thermal maturity. The method may also comprise determining at least an additional property of the geological formation based on the analysis of the at least one decontaminated rock sample, wherein the additional property is a mineralogical composition of the formation. DRIFTS spectroscopy enables in particular to measure both property with only one measurement.

Analyzing the at least one decontaminated sample may include analyzing the sample with an infrared spectroscopy, such as one or more of DRIFTS (Diffuse Reflectance Infrared Transform Spectroscopy), FTIR (Fourier Transform InfraRed) Spectroscopy, ATR (Attenuated Total Reflectance) spectroscopy, Laser Induced-Breakdown Spectroscopy (LIBS), Raman spectroscopy. It may be also a thermal analysis such as a TOC analysis as known in the art.

The method may also include performing additional analysis for determining additional properties, such as elemental or mineralogical composition. The additional analysis may also be an infrared analysis, a thermal analysis or an X-ray analysis, such as one or more of X-Ray Diffraction (XRD), X-Ray Fluorescence (XRF), Energy Dispersive X-Ray (EDX), Wavelength Dispersive X-Ray (WDX).

The disclosure also discloses a system for analyzing at least a rock sample extracted from a geological formation for analysis, wherein the system includes:
a. an oven installation having:
  i. at least a heating chamber for receiving the rock sample,
  ii. a heater for heating the chamber
  iii. a controlling unit so that the temperature inside the chamber is below 300° C. and
  iv. a flow generator for providing a flow of inert gas into the chamber,
b. an analyzer configured for analyzing at least one of the decontaminated samples in order to determine at least a property relative to non-volatile organic matter contained in the geological formation based on the analysis.

The invention claimed is:

1. A method of analyzing at least one rock sample extracted from a geological formation, wherein the method comprises:
heating the at least one rock sample disposed in a heating chamber under inert atmosphere with a temperature below or equal to 300° C. and with a flow of inert gas, wherein the flow of inert gas is configured to remove contaminants from the sample, and
analyzing at least one of the decontaminated rock samples and determining at least a property relative to non-volatile organic matter-contained in the geological formation based on the analysis, wherein the non-volatile organic matter includes kerogen.

2. The method of claim 1 includes grinding at least one of the samples once heated to form a powder and analyzing the at least one rock sample includes analyzing the powder.

3. The method according to claim 1, wherein the inert gas contains one or more of nitrogen, argon or helium.

4. The method according to claim 1, wherein an inlet pressure of the flowing inert gas is superior to atmospheric pressure.

5. The method according to claim 1, wherein the flow of inert gas is above 100 mL/min.

6. The method according to claim 1, wherein at least one of the rock samples is heated less than 30 minutes.

7. The method according to claim 1, wherein at least one of the rock samples is placed in a chamber during heating, wherein the volume of the heating chamber is below 0.1 L.

8. The method according to claim 7, wherein the method includes reducing the heating chamber volume with at least one spacer.

9. The method according to claim 1, wherein a plurality of rock samples are heated simultaneously in a plurality of respective heating chambers.

10. The method according to claim 1, wherein it is devoid of drying at least one of the rock samples between the heating and the analysis.

11. The method according to claim 1, wherein at least one of the rock samples weights between 1 and 50 g.

12. The method according to claim 1, wherein the method includes, before heating, collecting a plurality of rock fragments and sieving the rock fragments to select one or more rock samples.

13. The method according to claim 1, wherein the method includes, before heating, cleaning at least one of the rock samples, wherein the cleaning is performed with pressurized water or oil.

14. The method according to claim 1, wherein the property relative to the non-volatile organic matter includes total organic content (TOC) and/or thermal maturity.

15. The method according to claim 1, further comprising determining at least an additional property of the geological formation based on the analysis of the at least one decontaminated rock sample, wherein the additional property is a mineralogical composition of the formation.

16. The method according to claim 1, wherein at least one of the rock samples comprises drill cuttings recovered at the exit of a wellbore mixed with drilling fluid.

17. The method according to claim 16, wherein the method comprises heating at least one of the rock samples at a maximum temperature of 200° C. when the drilling fluid is water-based and/or heating at least one of the rock samples at a maximum temperature of 300° C. when the drilling fluid is oil-based.

18. The method according to claim 1, wherein analyzing the at least one decontaminated rock sample include analyzing the sample with one or more of an infrared spectroscopy or a thermal analysis.

19. The method according to claim 18, wherein the sample is analyzed with infrared spectroscopy with one or more of DRIFTS (Diffuse Reflectance Infrared Transform Spectroscopy), FTIR (Fourier Transform InfraRed) Spectroscopy, ATR (Attenuated Total Reflectance) spectroscopy, Laser Induced-Breakdown Spectroscopy (LIBS), or Raman spectroscopy.

20. A system for analyzing at least one rock sample extracted from a geological formation for analysis, wherein the system includes:
a. an oven installation having:
  i. at least a heating chamber under inert atmosphere for receiving the at least one rock sample,
  ii. a heater for heating the chamber,
  iii. a controlling unit configured to control the heater so that a temperature inside the chamber is below or equal to 300° C., and
  iv. a flow generator for providing a flow of inert gas into the chamber, wherein the flow of inert gas is configured to remove contaminants from the sample, and
b. an analyzer configured for analyzing at least one of the decontaminated samples and for determining at least a property relative to non-volatile organic matter contained in the geological formation based on the analysis, wherein the non-volatile organic matter includes kerogen.

* * * * *